United States Patent [19]

Hargrave et al.

[11] Patent Number: 5,547,951
[45] Date of Patent: Aug. 20, 1996

[54] PYRIDO[2,3-B][1,4]BENZOXAZEPIN (AND THIAZEPIN)-6(5H)-ONES AND -THIONES AND THEIR USE IN THE PREVENTION OR TREATMENT OF HIV-1 INFECTION

[75] Inventors: Karl D. Hargrave, Brookfield, Conn.; Gunther Schmidt, deceased, late of Munich, Germany, by Margaret Schmidt, legal representative

[73] Assignee: Boehringer Ingelheim Pharamceuticals, Inc., Ridgefield, Conn.

[21] Appl. No.: 292,154

[22] Filed: Aug. 17, 1994

Related U.S. Application Data

[63] Continuation of Ser. No. 131,112, Oct. 4, 1993, abandoned, which is a continuation of Ser. No. 955,391, Oct. 1, 1992, abandoned, which is a continuation of Ser. No. 823,391, Jan. 21, 1992, abandoned, which is a continuation of Ser. No. 584,411, Sep. 14, 1990, abandoned, which is a continuation of Ser. No. 400,248, Aug. 29, 1989, abandoned.

[51] Int. Cl.$^6$ .................... A61K 31/55; C07D 513/04; C07D 498/04
[52] U.S. Cl. .................... 514/211; 540/488; 546/292
[58] Field of Search ................ 540/488; 514/211

[56] References Cited

PUBLICATIONS

Wei et al, Nature, 373, p. 117 (1995).
Havlir, J. Infec. Disease 171, 537 (1995).
Connolly, Antimicro Agents & Chemother. 36, 245 (1992).
De Clercq, AIDS Res. & Human Net. 8, 119 (1992).
Mansuri, Chemtech, p. 564 (Sep. 1992).
Dr. Sandstrom letter, Jun. 19, 1990.
Anti viral Agents Bulletin 6, 162–163 (Jun. 1993).
Antiviral Agents Bulletin 6, 260 (Sep. 1993).
Antiviral Agents Bulletin 6, 228 (Aug. 1993).
Staal, AIDS Res. & Human Net. 9, 299 (1993).
Flether, Antimicrob. Agents & Chemo. 35, 2544 (1991).
Saari, J Med Chem 35, 3792 (1992).
Saunders, Drug Design & Disc. 8, 255 (1992).
Merck standby statement of Sep. 14, 1993.
Kamigata, Chem Abs 106, 66577g (1986).

*Primary Examiner*—Mark L. Berch
*Attorney, Agent, or Firm*—Robert P. Raymond; Alan R. Stempel; Mary-Ellen M. Devlin

[57] ABSTRACT

Compounds of the class of pyrido[2,3-b][1,4]benzoxazepin (and thiazepin)-6(5H)-ones and -thiones, having the following general structural formula

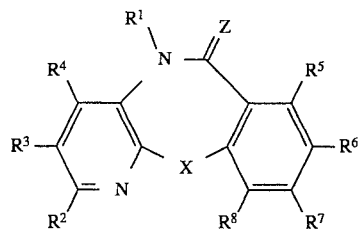

wherein either X or Z is sulfur and the other substituent is oxygen or both X and Z are sulfur, which are inhibitors of HIV-1 reverse transcriptase and useful in the treatment of HIV-1 infection. An exemplary compound is 2-chloro-5-(methylthioethyl)pyrido[2,3-b][1,4]benzoxazepin-6(5H)one.

6 Claims, No Drawings

PYRIDO[2,3-B][1,4]BENZOXAZEPIN (AND THIAZEPIN)-6(5H)-ONES AND -THIONES AND THEIR USE IN THE PREVENTION OR TREATMENT OF HIV-1 INFECTION

This is a continuation, application Ser. No. 08/131,112, filed Oct. 4, 1993, which is a continuation of application Ser. No. 955,391, filed Oct. 1, 1992, now abandoned, which is a continuation of application Ser. No. 823,391, filed Jan. 21, 1992, now abandoned, which is a continuation of application Ser. No. 584,411, filed Sep. 14, 1990, now abandoned, which is a continuation of application Ser. No. 400,248, filed Aug. 29, 1989, now abandoned.

FIELD OF THE INVENTION

The invention relates to novel pyrido[2,3-b][1,4]benzoxazepin (and thiazepin)-6(5H)-ones and -thiones, methods for preparing these compounds, the use of these and related but known compounds in the prevention or treatment of AIDS, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins.

The conversion of the RNA to DNA is accomplished through the use of the enzyme reverse transcriptase (RT), which is included within the infecting virion along with the RNA. Reverse transcriptase has three enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of The viral RNA. Next, acting as a ribonuclease, RT frees the DNA Just produced from the original viral RNA and then destroys the original RNA. Finally, acting as a DNA-dependent DNA polymerase, RT makes a second complementary, DNA strand, using the first DNA strand as a template. The two strands form double-stranded DNA, the form of DNA found in the host cell's genome, which is integrated into the host cell's genome by another enzyme, called an integrase.

Compounds which inhibit the enzymatic functions of HIV-1 reverse transcriptase will inhibit replication of HIV-1 in infected cells. Such compounds are useful in the prevention or treatment of HIV-1 infection in human subjects.

SUMMARY OF THE INVENTION

A first aspect of the invention comprises a method for preventing or treating HIV-1 infection which comprises administering, to a human exposed to or infected by HIV-1, a prophylactically or therapeutically effective amount of certain pyride[2,3-b][1,4]benzoxazepin (and thiazepin)-6(5H)-ones and thiones. Some of these compounds are novel and some are known. All possess inhibitory activity against HIV-1RT. A second aspect of the invention comprises novel pyrido[2,3-b][1,4]benzoxazepin (and thiazepin)-6(5H)-ones and -thiones. A third aspect of the invention comprises methods for making these novel compounds. A final aspect of the invention comprises pharmaceutical compositions suitable for the prevention or treatment of HIV-1 infection comprising the above mentioned compounds, both novel and known.

DETAILED DESCRIPTION OF THE INVENTION

A first aspect of the invention comprises a method for preventing or treating HIV-1 infection which comprises administering to a human, exposed to or infected by HIV-1, a prophylactically or therapeutically effective amount of a pyrido[2,3-b][1,4]benzoxazepin (or thiazepin)-6(5H)-one or -thione of the formula I

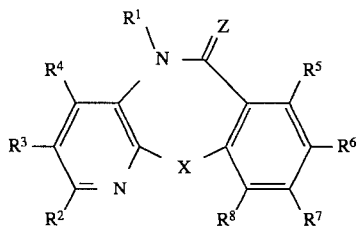

wherein,

X is oxygen or sulfur;

Z is oxygen or sulfur;

$R^1$ is alkyl of 1 to 4 carbon atoms, fluoroalkylmethyl of 1 to 3 fluorine atoms and 2 to 4 carbon atoms, mono- or dihalovinyl, alkenyl or alkynyl of 2 to 4 carbon atoms, 2-chloro-propen-3-yl, alkoxyalkyl or alkylthioalkyl of 2 to 3 carbon atoms, alkoxycarbonylalkyl of 3 to 4 carbon atoms, hydroxyalkylmethyl of 2 to 4 carbon atoms;

$R^2$ is hydrogen, methyl or chloro;

one of $R^3$ and $R^4$ is alkyl of 1 to 4 carbon atoms, aminoalkyl of 1 to 2 carbon atoms, mono- or dimethylaminomethyl, chloro, hydroxyalkyl of 1 to 4 carbon atoms, alkoxyalkyl wherein each alkyl moiety contains 1 to 2 carbon atoms, alkylthioalkyl wherein each alkyl moiety contains 1 to 2 carbon atoms, carboxyalkyl of 2 to 3 carbon atoms or methoxycarbonylmethyl, and the remaining group is hydrogen; or, $R^3$ and $R^4$ are both methyl or chloro when $R^2$ is hydrogen; or, $R^3$ and $R^4$ are both hydrogen when $R^2$ is methyl or chloro; or, $R^2$, $R^3$ and $R^4$ are each hydrogen; and, one of $R^5$, $R^6$, $R^7$ and $R^8$ is alkyl of 1 to 3 carbon atoms, hydroxyl, amino, methylamino, aminoalkyl of 1 to 2 carbon atoms, mono- or dimethylaminomethyl, hydroxyalkyl of 1 to 3 carbon atoms, alkoxyalkyl wherein each alkyl moiety contains 1 to 2 carbon atoms, alkylthioalkyl wherein each alkyl moiety contains 1 to 2 carbon atoms, carboxyalkyl of 2 to 3 carbon atoms, or alkoxycarbonylmethyl or 3 to 4 carbon atoms, one of the three remaining groups is hydrogen or methyl, and the remaining two groups are both hydrogen; or, two of $R^5$, $R^6$, $R^7$ and $R^8$ are methyl, and the remaining two groups are both hydrogen; or, $R^5$, $R^6$, $R^7$ and $R^8$ are each hydrogen.

In a subgeneric aspect, the invention comprises the above-described method wherein, in the compound of formula I, X is oxygen or sulfur;

Z is oxygen or sulfur;

$R^1$ is alkyl of 1 to 4 carbon atoms, fluoroalkylmethyl of 1 to 3 fluorine atoms and 2 to 4 carbon atoms, mono- or dihalovinyl, alkenylmethyl or alkynylmethyl of 2 to 4 carbon atoms, alkoxymethyl or alkylthiomethyl of 2 to 3 carbon atoms, methoxyethyl, or methylthioethyl;

$R^2$ is hydrogen or chloro;

one of $R^3$ and $R^4$ is hydrogen or alkyl of 1 to 4 carbon atoms; or, $R^3$ and $R^4$ are both methyl when $R^2$ is hydrogen; or, $R^2$, $R^3$, and $R^4$ are each hydrogen; and, one of $R^5$, $R^6$, $R^7$ and $R^8$ is alkyl of 1 to 3 carbon atoms, hydroxyl, amino, methylamino, aminoalkyl of 1 to 2 carbon atoms, mono- or dimethylaminomethyl, hydroxyalkyl of 1 to 3 carbon toms, alkoxyalkyl wherein each alkyl moiety contains 1 to 2 carbon atoms, alkylthioalkyl wherein each alkyl moiety contains 1 to 2 carbon atoms, alkoxycarbonylmethyl of 3 to 4 carbon atoms, one of the three remaining groups is hydrogen or methyl, and the remaining two groups are both hydrogen; or, two of $R^5$, $R^6$, $R^7$ and $R^8$ are methyl, and the remaining two groups are hydrogen; or, $R^5$, $R^6$, $R^7$ and $R^8$ are each hydrogen.

In a further subgeneric aspect, the invention comprises the above described method wherein, in the compound of formula I, X is oxygen or sulfur;

Z is oxygen;

$R^1$ is alkyl of 2 to 4 carbon atoms, alkenylmethyl of 3 to 4 carbon atoms, fluoroalkylmethyl of 1 to 3 fluorine atoms and 2 to 4 carbon atoms, or mono-or dihalovinyl;

$R^2$, $R^3$, $R^4$, $R^6$, $R^7$ and $R^8$ are each hydrogen; and, $R^5$ is hydrogen or amino.

A still further subgeneric aspect of the invention comprises the above-described method wherein, in the compound of formula I, X is oxygen or sulfur;

Z is oxygen;

$R^1$ is propyl, allyl, methylthiomethyl or methylthtoethyl;

$R^2$ is chloro; and $R^3$ through $R^8$ are each hydrogen.

A preferred compound which can be used in the practice of the method is 2-chloro-5-methylthiomethyl-pyrido[2,3-b][1,4]benzoxazepin-6(5H)-one.

Compounds of formula I may, if desired, be converted into their pharmaceutically acceptable acid salts by conventional methods. The invention also comprises the use of such pharmaceutically acceptable salts.

Examples of inorganic and organic acids which may form pharmaceutically acceptable acid addition salts with compounds of formula I are the following: hydrochloric acid, hydrobromic acid, sulfuric acid, phosphoric acid, nitric acid, tartaric acid, citric acid, methanesulfonic acid and the like.

Examples of inorganic and organic bases which may form pharmaceutically acceptable salts with compounds of formula I having acidic substituents capable of forming such salts are the following: sodium, hydroxide, potassium hydroxide, calcium hydroxide, tromethamine and ammonia.

The above described compounds of formula I inhibit HIV-1 reverse transcriptase and thereby inhibit HIV-1 replication, making them useful in the method which constitutes the first aspect of the invention.

In carrying out this method, the compounds formula I may be administered in single or divided doses by the oral, parenteral or topical routes. A suitable oral dosage for such compounds would be in the range of about 10 to 500 mg per day. In parenteral formulations, a suitable dosage unit may contain from 1 to 50 mg of said compounds, whereas for topical administration, formulations containing 0.01 to 1% active ingredient are preferred. It should be understood, however, that the dosage administration from patient to patient will vary and the dosage for any particular patient will depend upon the clinician's Judgement, who will use as criteria for fixing a proper dosage the size and condition of the patient as well as the patient's response to the drug.

When such compounds are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkyleneglycols, petroleum jelly and the like. The pharmaceutical preparations can be prepared in a conventional manner and finished dosage forms can be solid dosage forms, for example, tablets, degrees, capsules, and the like, or liquid dosage forms, for example, solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers, such as polyethylene glycol.

For parenteral use, it is preferred to administer such compounds in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds can also be administered as solutions for nasal applications which may contain, in addition to the compounds, suitable buffers, tonicity adjusters, microbial preservatives, antioxidants and viscosity- increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chlorobutanol or phenylethyl alcohol.

Additionally, such compounds can be administered by suppository.

In its composition of matter aspect, the invention comprises novel compounds of formula I, wherein $R^1$ through $R^8$ are as set forth above and either X or Z or both X and Z are sulfur, as well as pharmaceutically acceptable acid addition salts thereof. In addition, the invention comprises the novel compound 2-chloro-5-(methylthiomethyl)pyrido[2,3-b][1,4]benzoxazepin-6(5H)one.

Compounds of formula I, can be prepared according to the following general methods A, B, C, and D.

Method A

Compounds of Formula I, wherein Z is oxygen and wherein X and $R^1$–$R^8$ have the meanings defined above, may be obtained, for example by converting a compound of the formula II

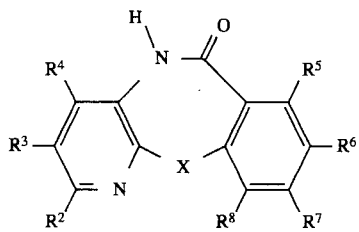
II wherein $R^2$–$R^8$ are as defined above, into the corresponding alkali or alkaline earth methyl compounds of the formula III

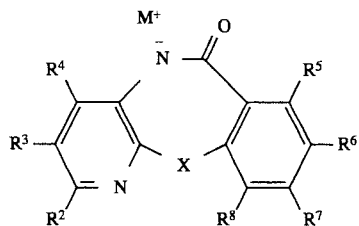
III wherein $R^2$–$R^8$ are as defined above and subsequently reacting, without isolation, this alkali metal compound with a reactive alkylating or acylating reagent of the formula IV $R^1Y$  IV wherein $R^1$ has the meanings defined above and Y is a suitable leaving group such as chloride, bromide, iodide, an alkyl or arylsulfonate, or an alkyl- or arylcarbonyloxy group, under well known alkylating or acylating conditions.

It will be obvious to those skilled in the art that the presence of nucleophilic substituents in compounds of formula II will require the use of an intermediate having substituents which are, other than the 5-position nitrogen, not nucleophilic but which can be derivatized to yield the required group. For example, amino or monoalkylamino substituents are preferably obtained by alkylating or acylating an intermediate of formula II having nitro group(s) at the desired positions, and subsequently reducing the nitro group(s), and alkylating, if appropriate, to yield the final product.

Method B

Compounds of formula II wherein Z is oxygen and X and $R^2$–$R^8$ are as defined above may be obtained by cyclization of compounds of formula V

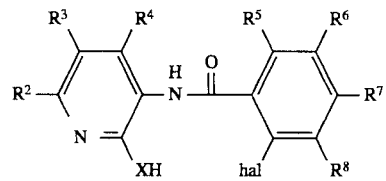
V wherein X and $R^1$–$R^8$ are as defined above and hal is fluorine, chlorine, bromine or iodine, preferably in the presence of an inorganic base, such as sodium or potassium hydride, lithium alkyls such as n-butyl lithium, sodium or potassium hydroxide, or in the presence of an organic base such as quinoline or 4-(N,N-dimethylamino)pyridine, at ambient or elevated temperatures, preferably 80° to 175° C., up to the boiling point of the reaction mixture. Suitable solvents include inert aprotic solvents such as sulfolane or dimethylformamide.

The diphenylamides of formula V may be obtained, for example, by condensing suitably substituted ortho-halobenzoic acid chlorides of the formula VI

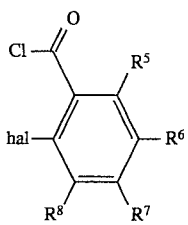
VI wherein hal may be fluorine, chlorine, bromine or iodine and $R^5$ and $R^8$ are as defined above, with ortho-amino-phenols (or thiophenols) of the formula VII

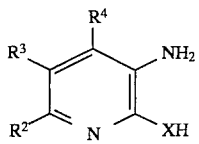
VII wherein X, and $R^1$–$R^4$ are as defined above, under well-known reaction conditions. Depending upon the reaction conditions and the nature of X and $R^2$–$R^8$, tricyclic compounds of the formula II may be formed in one step, without the isolation of the amide of formula V, by the condensation of compounds of the formulas VI and VII. This single-step formation of the tricyclic compounds is most readily effected when X is sulfur and at elevated temperatures, especially in the range of 125°–200° C.

Method C

An alternative procedure to obtain compounds of the formula II is to condense suitably substituted ortho-carboxyphenols (or thiophenols) of the formula VIII

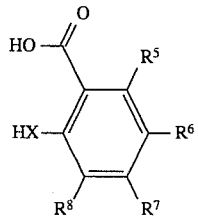
VIII wherein X and $R^5$–$R^8$ are as defined above with suitably substituted 2-halo-3-aminopyridines of the formula IX

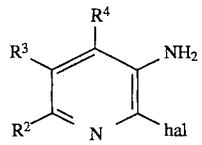
IX wherein hal is fluorine, chlorine, bromine or iodine and $R^2$–$R^4$ are as defined above. The reaction is carried out under nitrogen at the boiling point in an inert solvent such as trichlorobenzene.

Method D

Thiolactams of the formula I, wherein X and $R^1$–$R^8$ are as defined above, can be obtained by treatment of lactams of the formula I with sulfurating reagents such as 2,4-bis(4-methoxyphenyl)-1,3-dithia-2-4-.diphosphetane-2,4-disulfide, bis(tricyclohexyltin)sulfide, bis(tri-n-butyltin)sulfide, bis(triphenyltin)sulfide, bis(trimethylsilyl)sulfide, and phosphorous pentasulfide. The reaction is generally carried out under anhydrous conditions, in inert organic solvents such as carbon disulfied, benzene, or toluene, at room temperature or, preferably, higher temperatures up to the boiling point of the reaction mixture. When using the above mentioned tin or silyl sulfides it is preferable to carry out the sulfurizatton reaction in the presence of a Lewis acid such as boron trichloride.

It will be obvious to those skilled in the art that the presence of another carbonyl moiety in a compound of formula I, for example, a compound wherein Z is oxygen and any of $R^3$ to $R^8$ is alkoxycarbonylalkyl, may require that the ester be protected via known methods or that the ester moiety be formed subsequent to the sulfurization step.

As stated before, the compounds provided by the invention inhibit the enzymatic activity of HIV-1 RT. Based upon testing of these compounds, as described below, it is known that they inhibit the RNA-dependent DNA polymerase activity of HIV RT. It is also believed that they also inhibit the DNA-dependent DNA polymerase activity of HIV RT.

Utilizing the Reverse Transcriptase (RT) Assay described below, compounds can be tested for their ability to inhibit the RNA-dependent DNA polymerase activity of HIV RT. Certain specific compounds, described in the Examples which appear below, were so tested. The results of this testing appear in Table I, below.

REVERSE TRANSCRIPTASE (RT) ASSAY

Assay Theory

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay which has been previously described (2), and is based upon the observation that reverse transcriptase is able to use a synthetic template [poly r(C) primed with oligo d(G)] to transcribe a radio-labelled, acidprecipitable DNA strand utilizing $^3$H-dGTP as a substrate.

Materials a) Preparation of the enzyme

Reverse transcriptase enzyme from the LAV strain of Human Immuno- deficiency Virus (HIV-1) (1) was isolated from the bacterial strain JM109 (3) expressing the DNA clone pBRTprtl+ (2) which is under the control of the lac promotor in the expression vector pIBI21 (4). An overnight culture grown in 2XYT medium (37° C., 225 rpm) (5) supplemented with 100 µg/ml ampicillin for positive selection is inoculated at a 1:40 dilution into M9 medium supplemented with 10µg/ml thiamine, 0.5% casamino acids, and 50 µg/ml ampicillin (5). The culture is incubated (37° C., 225 rpm) until it reaches an OD540 of 0.3–0.4. At that time the repressor inhibitor IPTG (isopropyl b-D-thiogalactopyranoside) is added to 0.5 mM and incubated for 2 additional hours. Bacteria are pelleted, resuspended in a 50mM Tris, 0.6mM EDTA, 0.375 M NaGl buffer and digested by the addition of lysozyme (1 mg/ml) for 30 minutes on ice. The cells are lysed by the addition to 0.2% NP-40 and brought to 1 M NAGl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5mM DTT, 0.1% NP-40, 0.1M NaCl, and 50% glycerol) and stored at –70° C. for further use.

b) Composition of 2X concentrated stock reaction mixture

| Stock Reagent | 2X Mix Concentration |
| --- | --- |
| 1M Tris pH 7.4 | 100 mM |
| 1M Dithiothrietol | 40 mM |
| 1M NaCl | 120 mM |
| 1% Nonidet P-40 | 0.1% |
| 1M MgCl | 4 mM |
| [poly r(C)/oligo d(G)](5:1) | 2 µg/ml |
| $^3$H-dGTP (81 µM) | 0.6 µM |

Assay Procedure

The 2X concentrated stock reaction mixture is aliquoted and stored at –20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 µl/well; 3 wells/compound). The HIV RT enzyme is thawed, diluted in 50 mM Tris pH 7.4 so that fifteen µl of diluted enzyme contain 0.001 Unit (one unit is that amount of enzyme to transform 1 micromole of substrate per minute at 25° C.), and 15 µ are dispensed per well. Twenty µl of 0.12–0.5M EDTA are added to the first three wells of the microtiter plate. EDTA thelares the $Mg^{++}$ present and prevents reverse transcription. This group serves as background polymerization which is subtracted from all other groups. Twenty-five µl of the 2X reaction mixture are added to all wells and the assay is allowed to incubate at room temperature for 60 minutes. The assay is terminated by precipitating the DNA in each well with 50 µl of 10% trichloracetic acid (TCA) in 1% sodium pyrophosphate. The microtiter plate is incubated for 15 minutes at 4° C. and the precipitate is fixed onto #30 glass fiber paper (Schletcher & Schuell) using a Skatron semi- automatic harvester. The filters are then washed with additional 5% TCA containing 1% sodium pyrophosphate, rinsed with 70% aqueous ethanol, dried, and transferred to scintillation vials (6). Each vial receives 2 mls of scintillation cocktail and is counted in a Beckman beta counter.

Calculations for percent inhibition are as follows $$\% \text{ inhibition} = \frac{\text{CPM Mean Test Value} - \text{CPM Mean Control Value} \times 100}{\text{CPM Mean Control Value}}$$

References

1. Benn, S., et al., SCIENCE 230:949, 1985
2. Farmerie, W.G. et. al., SCIENCE 236:305, 1987
3. Yanisch-Perron, C., Viera, J., and Messing, J., GENE 33:103, 1985
4. International Biotechnologies, Inc., New Haven, Conn. 06535
5. Maniatis, T, Fritsch, E.F., and J. Sambrook, eds. MOLECULAR CLONING: A LABORATORY MANWAL, Cold Spring Harbor Laboratory, 1982
6. Spira, T., et. al. J. Clinical Microbiology, 25:97, 1987.

In order to roughly assess the cytotoxicity of the compounds of formula I, several were tested in the MTT Cellular Cytotoxicity Assay described below. The results of this testing are reported in Table I, below. Compounds having a relatively high $EC_{50}$ are preferred.

MTT ASSAY FOR CELLULAR CYTOTOXICITY

Assay Theory

The MTT [3-(4,5-dimethylthiazol-2yl)-2,5 diphenyl tetrazolium bromide] assay is based on cleavage of tetrazolium bromide by metabolically active cells, resulting in a highly quantitative blue color. This assay has been previously described (1) but has been optimized for the purposes of the testing reported herein.

Assay Method

The H9 cell line (2), an established human lymphoma suspension cell line grown in RPMI 1640 supplemented with 10% fetal bovine serum is used as the target cell line in the assay. Cells (100µl) are plated in microtest plate wells at a concentration of $10^5$ cells per ml in the presence of varying concentrations of inhibitor. The cells are incubated at 37° C in a humidified $CO_2$ incubator. Five days later, 20 µl of MTT (5 mg/ml in RPMI 1640, sonicated, 0.2 micron filtered, and stored at 4° C.) is added to each well. After 4 hours additional incubation at 37° 60 µl of Triton-X is added to each well and thoroughly mixed to aid the solubiltzation of the crystals. Absolute ethanol (5µ) is added to remove bubbles, and the mixture is incubated for 30 minutes at 60° C. and immediately read on a plate reader (Dynatech) at a wavelength of 570 nm.

Data from this assay are used to generate a nonlinear regression analysis which yields an $EC_{50}$.

References
1. Mosmann, Tim, J. Immunol. Methods, 65:55, 1983.
2. Jacobs, J.P., 3. Natl. Cancer Inst., 34:231, 1965.

TABLE I

| Compound of Example | RT Inhibition (% @ 10 µg/ml) | Cytotoxity Assay ($EC_{50}$, µg/ml) |
| --- | --- | --- |
| 1 | 99 | 20 |
| 2 | 96 | NT |
| 3 | 30 | " |
| 4 | 50 | " |
| 5 | 83 | NT |
| 6 | 50 | " |
| 7 | 66 | " |
| 8 | 47 | " |
| 9 | 39 | " |
| 10 | 84 | " |
| 11 | 30 | " |
| 12 | 49 | " |

Note: NT = not tested

The following examples further illustrate the present invention and will enable others skilled in the art to understand the invention more completely. It should be understood, however, that the invention is not limited to the particulars given in the examples.

EXAMPLE 1

2-Chloro-5-(methylthioethyl)pyrido[2,3-b][1,4]benzoxazepin-6(5H)-one (a) 2,6-Dichloro-3-(2'-hydroxybenzoyl)aminopyridine A suspension of 60.3g (0.37 mole) 2,6-dichloro-3-aminopyridine and salicylic acid 61g (0.44 mole) in 300 mL of toluene were heated to reflux for one hour. The reaction mixture was cooled at 90° C. and 34.2 ml (0.47 mole) of thionyl chloride was slowly added. After the addition the reaction mixture was refluxed for 3 hours, then cooled to room temperature. To the reaction mixture was added a solution containing 20g NaOH in 740 mL of $H_2O$. The organic phase was separated and washed with water. The organic phase was treated with charcoal, filtered and the filtrate treated with $CO_2$, the brownish precipitate was filtered off. Recrystallization from isopropyl alcohol gave 63.3g (60.5%) mp 179°–186° C.

(b) 2-Chloro-pyrido[2,3-b][1,4]-benzoxazepin-6(5H)-one

A solution of 11.6g (0.039 mole) of 2,6-dichloro-3-(2'-hydroxybenzoyl)aminopyridine and 2.95g (0.04 mol) potassium methoxide in 60 mL of water was concentrated under vacuum. The rest of the water was removed by the addition of ethanol followed by evaporation to dryness. The residue was dissolved in 40 mL of tetraethyleneglycoldiethyl ether. The mixture was heated with stirring to 220° for 45 minutes. The resulting precipitate was cooled and poured into dilute NaOH solution and filtered, to give 1.8 g. Recrystallizatlon from n-propanol, DMF and ether yielded 4.7g, of 2-chloro-pyrido[2,3-b][1,4]benzoxazepin-6(5H)-one, mp 311°–313° C. (total yield 35%).

(c) 2-Chloro-5-(methylthioethyl)pyrido[2,3-b][1,4]benzoxazepin-6(5H)-one

To as suspension of 17.0g (0.069 mole) 2-Chloropyrido [2,3-b][1,4]benzoxazepin-6(5H)-one and 150 mL of N,N-dimethylacetamide was added 9.8g of sodium hydride (50%). The mixture was warmed to 60° C. for 30 minutes. To the reaction mixture 12.2g (0.11 mole) of 2-chloroethylmethylsulfide was added dropwise. The mixture was heated to 120° C. for 4 hours, then cooled to room temperature and poured into water. The crude product was purified by column chromatography using silica gel and then recrystallized from petroleum ether/benzene to yield 17.3g (78% yield) of 2-chloro-5-(methylthioethyl)pyrido[2,3-b][1,4] benzoxazepin-6(5H)-one, m.p. 126°–128° C.

EXAMPLE 2

5-Allyl-2-chloropyrido[2,3-b][1,4]benzoxazepin-6(5H)-one

The title compound was prepared in manner analogous to the procedure described in Example 1. It was recrystallized from ethanol to form a crystalline solid, m.p. 110°–112° C.

EXAMPLE 3

5-Methylpyrido[2,3-b][1,4]benzoxazepin-6(5H)-one

The title compound was prepared in manner analogous to the procedure described in Example 1. It was recrystallized from ethyl acetate/cyclohexane (1:1) to form a crystalline solid, m.p. 137°–139° C.

EXAMPLE 4

5-Sec-butylpyrido[2,3-b][1,4]benzoxazepin-6(5H) -one

The title compound was prepared in manner analogous to the procedure described in Example 1. It was recrystallized from aqueous acteonitrile to form a crystalline solid, m.p. 137°–138° C.

EXAMPLE 5

5-Ethyl-10-methylpyrido[2,3-b][1,4]benzoxazepin-6(5H)-one

The title compound was prepared in manner analogous to the procedure described in Example 1. It was recrystallized from petroleum ether to form a crystalline solid, m.p. 74°–76° C.

EXAMPLE 6

8-Amino-5-methylpyrido[2,3-b][1,4]benzoxazepin-6(5H)-one

The title compound was prepared in manner analogous to the procedure described in Example 1. It was recrystallized from isopropanol to form a crystalline solid, m.p. 158°–160° C.

EXAMPLE 7

5-(2-Chloro-2-propen-1-yl)pyrido[2,3-b][1,4]benzoxazepin-6(5H)-one

The title compound was prepared in manner analogous to the procedure described in Example 1. It was recrystallized from cyclohexane to form a crystalline solid, m.p. 106°–108° C.

EXAMPLE 8

5-(2-Methyl-2-propen-1-yl)pyrido[2,3-b][1,4]benzoxazepin-6(5H)-one

The title compound was prepared in manner analogous to the procedure described in Example 1. It was recrystallized from cyclohexane to form a crystalline solid, m.p. 106°–107° C.

EXAMPLE 9

5-(2-Buten-1-yl)pyrido[2,3-b][1,4]benzoxazepin-6(5H)-one

The title compound was prepared in manner analogous to the procedure described in Example 1. It was recrystallized from isopropanol to form a crystalline solid, m.p. 79°–81° C.

EXAMPLE 10

5-Allyl-10-methylpyrido[2,3-b][1,4]benzoxazepin-6(5H)-one

The title compound was prepared in manner analogous to the procedure described in Example 1. It was recrystallized from cyclohexane to form a crystalline solid, m.p. 58°–60° C.

EXAMPLE 11

5-Ethyl-9-methylpyrido[2,3-b][1,4]benzoxazepin-6(5H)-one

The title compound was prepared in manner analogous to the procedure described in Example 1. It was recrystallized from ligroin to form a crystalline solid, m.p. 88°–90° C.

EXAMPLE 12

8-Methyl-5-propionylpyrido[2,3-b][1,4]benzoxazepin-6(5H)-one

The title compound was prepared in manner analogous to the procedure described in Example 1. It was recrystallized from ethanol to form a crystalline solid, m.p. 142°–145° C.

EXAMPLE A

Capsules or Tablets

| A-1 | | A-2 | |
| --- | --- | --- | --- |
| Ingredients | Quantity | Ingredients | Quantity |
| Compound of Example 1 | 50 mg | Example 1 | 50 mg |
| Starch | 160 mg | Dicalcium Phosphate | 160 mg |
| Microcrys. Cellulose | 90 mg | Microcrys. Cellulose | 90 mg |
| Sodium Starch Gluctate | 10 mg | Stearic acid | 5 mg |
| Magnesium Stearte | 2 mg | Sodium Starch Glycolate | 10 mg |
| Fumed colloidal silica | 1 mg | Fumed colloidal silica | 1 mg |

The compound of Example 1 is blended into a powder mixture with the premixed exipient materials as identified above with the exception of the lubricant. The lubricant is then blended in and the resulting blend compressed into tablets or filled into hard gelatin capsules.

EXAMPLE B

Parenteral Solutions

| Ingredients | Quantity |
| --- | --- |
| Compound of Example 1 | 500 mg |
| Ethanol | 25 ml |
| Water for injection | q.s. to 100 ml |

Compound of Example 1 is added to the ethanol and mixed until the solution is clear. Water is added and the resulting solution is then filtered into the appropriate vials or ampoules and sterilized by autoclaving.

EXAMPLE C

Nasal Solutions

| Ingredients | Quantity |
| --- | --- |
| Compound of Example 1 | 500 mg |
| Propylene glycol | 30 ml |
| Benzalkonium chloride | 200 mg |
| EDTA | 200 mg |
| Water | q.s. to 100 ml |

The excipient materials are mixed and thereafter the compound of Example 1 is added and mixing is continued until the solution is clear. The water is added and the resulting solution is then filtered into the appropriate vials or ampoules.

We claim:

1. A compound of the formula I

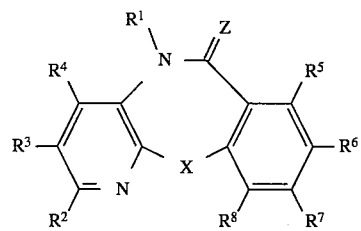

wherein,
either X or Z is sulfur and the other substituent is oxygen or both X and Z are sulfur;

$R^1$ is alkyl of 1 to 4 carbon atoms, fluoroalkylmethyl of 1 to 3 fluorine atoms and 2 to 4 carbon atoms, mono- or dihalovinyl, alkenyl or alkynyl of 2 to 4 carbon atoms, 2-chloro-propen-3-yl, alkoxyalkyl or alkylthioalkyl of 2 to 3 carbon atoms, alkoxycarbonylalkyl of 3 to 4 carbon atoms, or hydroxyalkylmethyl of 2 to 4 carbon atoms;

$R^2$ is hydrogen, methyl or chloro;

one of $R^3$ and $R^4$ is alkyl of 1 to 4 carbon atoms, aminoalkyl of 1 to 2 carbon atoms, mono- or dimethylaminomethyl, chloro, hydroxyalkyl of 1 to 4 carbon atoms, alkoxyalkyl wherein each alkyl moiety contains 1 to 2 carbon atoms, alkylthioalkyl wherein each alkyl moiety contains 1 to 2 carbon atoms, carboxyalkyl of 2 to 3 carbon atoms, or methoxycarbonylmethyl, and the remaining group is hydrogen; or, $R^3$ and $R^4$ are both methyl or chloro when $R^2$ is hydrogen; or, $R^3$ and $R^4$ are both hydrogen when $R^2$ is methyl or chloro; or, $R^2$, $R^3$ and $R^4$ are each hydrogen; and, one of $R^5$, $R^6$, $R^7$ and $R^8$ is alkyl of 1 to 3 carbon atoms, hydroxyl, amino, methylamino, aminoalkyl of 1 to 2 carbon atoms, mono- or dimethylaminomethyl, hydroxyalkyl of 1 to 3 carbon atoms, alkoxyalkyl wherein each alkyl moiety contains 1 to 2 carbon atoms, alkylthioalkyl wherein each alkyl moiety contains 1 to 2 carbon atoms, carboxyalkyl of 2 to 3 carbon atoms, or alkoxycarbonylmethyl or 3 to 4 carbon atoms, one of the three remaining groups is hydrogen or methyl, and the remaining two groups are both hydrogen; or, $R^5$, $R^6$, $R^7$ and $R^8$ are each hydrogen;

or a pharmaceutically acceptable acid addition salt thereof.

2. 2-Chloro-5-(methylthioethyl)-pyrido[2,3-b][1,4]benzoxazepin-6(5H)one.

3. A compound of formula I, as set forth in claim 1, wherein, $R^1$ is alkyl of 1 to 4 carbon atoms, fluoroalkylmethyl of 1 to 3 fluorine atoms and 2 to 4 carbon atoms, mono- or dihalovinyl, alkenylmethyl or alkynylmethyl of 2 to 4 carbon atoms, alkoxymethyl or alkylthiomethyl of 2 to 3 carbon atoms, methoxyethyl, or methylthicethyl;

$R^2$ is hydrogen or chloro;

one of $R^3$ and $R^4$ is hydrogen or alkyl of 1 to 4 carbon atoms; or, $R^3$ and $R^4$ are both methyl when $R^2$ is hydrogen; or, $R^2$, $R^3$, and $R^4$ are each hydrogen; and, one of $R^5$, $R^6$, $R^7$ and $R^8$ is alkyl of 1 to 3 carbon atoms, hydroxyl, amino, methylamino, aminoalkyl of 1 to 2 carbon atoms, mono- or dimethylaminomethyl, hydroxyalkyl or 1 to 3 carbon toms, alkoxyalkyl wherein each alkyl moiety contains 1 to 2 carbon atoms, alkylthioalkyl wherein each alkyl moiety contains 1 to 2 carbon atoms, alkoxycarbonylmethyl of 3 to 4 carbon atoms, one of the three remaining groups is hydrogen or methyl, and the remaining two groups are both hydrogen; or, two of $R^5$, $R^6$, $R^7$ and $R^8$ are methyl, and the remaining two groups are hydrogen; or, $R^5$, $R^6$, $R^7$ and $R^8$ are each hydrogen.

4. A compound of formula I, as set forth in claim 1, wherein $R^1$ is alkyl of 2 to 4 carbon atoms, alkenylmethyl of 3 to 4 carbon atoms, fluoroalkylmethyl of 1 to 3 fluorine atoms and 2 to 4 carbon atoms, or mono-or dihalovinyl;

$R^2$, $R^3$, $R^4$, $R^6$, $R^7$ and $R^8$ are each hydrogen; and, $R^5$ is hydrogen or amino.

5. A compound of formula I, as set forth in claim 1, wherein $R^1$ is propyl, allyl, methylthiomethyl or methylthioethyl;

$R^2$ is chloro; and $R^3$, $R^4$, $R^6$, $R^7$ and $R^8$ are each hydrogen.

6. A pharmaceutical composition suitable for the prevention or treatment of HIV-1 infection which comprises a prophylactically or therapeutically effective amount of a compound of formula I, as set forth in claims 1, 3, 4, 5 or 2 and a pharmaceutically acceptable carrier.

* * * * *